(12) United States Patent
Plunkett et al.

(10) Patent No.: US 10,898,378 B2
(45) Date of Patent: Jan. 26, 2021

(54) REFLEX COAXIAL ILLUMINATOR

(71) Applicant: ELLEX MEDICAL PTY LTD, Mawson Lakes (AU)

(72) Inventors: Malcolm Plunkett, Adelaide (AU); Wei Xia, Adelaide (AU)

(73) Assignee: ELLEX MEDICAL PTY LTD, Mawson Lakes (AU)

( * ) Notice: Subject to any disclaimer, the term of this patent is extended or adjusted under 35 U.S.C. 154(b) by 102 days.

(21) Appl. No.: 16/275,249

(22) Filed: Feb. 13, 2019

(65) Prior Publication Data

US 2019/0209371 A1    Jul. 11, 2019

Related U.S. Application Data

(62) Division of application No. 14/403,155, filed as application No. PCT/AU2013/000546 on May 23, 2013, now Pat. No. 10,369,051.

(30) Foreign Application Priority Data

May 30, 2012    (AU) ................ 2012902250

(51) Int. Cl.
| | | |
|---|---|---|
| *A61F 9/008* | (2006.01) | |
| *G02B 7/182* | (2006.01) | |
| *G02B 27/14* | (2006.01) | |
| *F21V 14/04* | (2006.01) | |
| *G02B 26/08* | (2006.01) | |

(52) U.S. Cl.
CPC ............. *A61F 9/008* (2013.01); *F21V 14/04* (2013.01); *G02B 7/1827* (2013.01); *G02B 26/0816* (2013.01); *G02B 27/14* (2013.01)

(58) Field of Classification Search
CPC .......... A61F 9/008–2009/00897; F21V 14/04; G02B 26/0816; G02B 27/14; G02B 7/1827; A61B 18/20–18/28
USPC ............................................ 606/4–6, 10–12
See application file for complete search history.

(56) References Cited

U.S. PATENT DOCUMENTS

| | | | |
|---|---|---|---|
| 3,720,454 | A | 3/1973 | Inderhees |
| 4,520,824 | A | 6/1985 | Swaniger et al. |
| 6,286,960 | B1 | 9/2001 | Tomita |
| 6,419,627 | B1 | 7/2002 | Nun |
| 10,369,051 | B2 | 8/2019 | Plunkett et al. |

(Continued)

FOREIGN PATENT DOCUMENTS

| | | |
|---|---|---|
| DE | 10 2005 032946 A1 | 2/2006 |
| WO | WO 90/09141 A2 | 8/1990 |

(Continued)

OTHER PUBLICATIONS

EPO Application No. 13797612.2 (Published as EP2854730), Supplementary European Search Report and European Search Opinion dated Dec. 23, 2015.

(Continued)

*Primary Examiner* — Jonathan T Kuo
(74) *Attorney, Agent, or Firm* — Alston & Bird LLP

(57) ABSTRACT

A mirror for an ophthalmic laser treatment device that is movable on an axis from a position in a treatment laser beam path to a position out of the treatment laser beam path. The mirror reflects light from a light source into the eye of a patient. The mirror is biased towards a position in the path and is moved out of the path by an actuator just long enough for the laser treatment to be applied and without noticeable interruption to viewing by a user.

22 Claims, 5 Drawing Sheets

(56) References Cited

U.S. PATENT DOCUMENTS

| | | |
|---|---|---|
| 2003/0120325 A1 | 6/2003 | Fujisaka et al. |
| 2004/0059321 A1 | 3/2004 | Knopp et al. |
| 2004/0246575 A1 | 12/2004 | Tonooka |
| 2005/0033389 A1 | 2/2005 | Auld et al. |
| 2008/0058734 A1 | 3/2008 | Hanft et al. |
| 2019/0282403 A1 | 9/2019 | Barrett et al. |

FOREIGN PATENT DOCUMENTS

| | | |
|---|---|---|
| WO | WO 2013/177611 A1 | 12/2013 |
| WO | WO 2018/068081 A1 | 4/2018 |

OTHER PUBLICATIONS

U.S. Appl. No. 14/403,155, Final Office Action dated Jun. 15, 2017.
U.S. Appl. No. 14/403,155, Final Office Action dated Oct. 18, 2018.
U.S. Appl. No. 14/403,155, Non-Final Office Action dated Mar. 7, 2018.
U.S. Appl. No. 14/403,155, Non-Final Office Action dated Dec. 15, 2016.
U.S. Appl. No. 14/403,155, Notice of Allowance and Examiner Initiated Interview Summary dated Mar. 26, 2019.
U.S. Appl. No. 14/403,155, Requirement for Restriction/Election dated Jul. 11, 2016.
WIPO Application No. PCT/AU2013/000546, PCT International Preliminary Report on Patentability dated Sep. 24, 2014.
WIPO Application No. PCT/AU2013/000546, PCT International Search Report dated Aug. 16, 2013.
WIPO Application. No. PCT/AU2013/000546, PCT Written Opinion of the International Searching Authority dated Aug. 16, 2013.

REFLEX COAXIAL ILLUMINATOR

CROSS-REFERENCE TO RELATED APPLICATIONS

This application is a divisional of U.S. Ser. No. 14/403,155 filed Nov. 21, 2014, which is the US national stage of PCT/AU2013/000546 filed May 23, 2013, incorporated by reference in its entirety for all purposes, which claims the benefit of AU 2012902250 filed May 30, 2012.

FIELD OF THE INVENTION

The present invention relates to the field of optics. More particularly, the invention relates to an optical element for illumination of the eye in an ophthalmic laser device.

BACKGROUND TO THE INVENTION

Lasers are well accepted as essential tools for ophthalmic treatments. A laser treatment device requires four basic elements in order to effectively deliver laser energy into the eye for medical treatment. The four essential elements are:

An illuminator delivering light to the target treatment area to assist viewing;
A microscope (preferable binocular) for viewing the target treatment area;
Optics to deliver aiming beams to the target treatment area to assist with accurate targeting of the treatment; and
Optics to deliver the treatment laser beam to the target treatment area.

It is known to use a slit lamp to provide the illumination and to view the target treatment area with a binocular microscope. It is also known to use a dichroic mirror to reflect the treatment laser beam and aiming beams into the microscope viewing path. In order to deliver the illumination, aiming beams and treatment beams without blocking the binocular viewing path, it is usual to provide the illumination from a position outside the main optical path. The aiming beams, treatment laser beam and viewing path are focussed by an objective lens. A typical prior art arrangement is shown in FIG. 1.

The arrangement in FIG. 1 is functional but does not provide illumination of the treatment area coaxially with the viewing or laser paths. This is mot usually a problem for anterior treatments of the eye since the illumination adequately illuminates the treatment area. For posterior treatment areas there is a problem since the optical path for the treatment laser beam, aiming beams, illumination and viewing must pass through the aperture created by the iris. A typical dilated iris is about 7.8 mm and is located about 20 mm from the retina. The angles are such that for treatment of the posterior of the eye virtually coaxial delivery of the treatment laser beam, aiming laser beam, illumination and viewing is required. This is not possible with the geometry of FIG. 1.

One approach to overcome this problem has been to use dual illumination mirrors placed between the binocular viewing paths (JP10328226) with a small spacing to allow laser beams to be delivered between them, thus providing almost coaxial illumination. The problem with this approach is that the illumination is not quite coaxial and the reduced aperture for the treatment laser beam restricts the laser beam diameter.

The restricted treatment laser beam diameter is a particular problem for short pulse photo-disruptor lasers that require a full cone angle of 14 to 18 degrees and a working distance of 90 to 100 mm. These parameters require the laser beam emitted from the microscope to have a diameter approximately the same diameter as the viewing objective lens, so that coaxial illumination with the existing arrangements is not possible without blocking a portion of the treatment laser beam.

SUMMARY OF THE INVENTION

In one form, although it need not be the only or indeed the broadest form, the invention resides in a reflex coaxial illuminator for an ophthalmic laser device comprising a reflex mirror movable on an axis from a position in a treatment laser beam path to a position out of the treatment laser beam path.

Suitably the reflex mirror is rotated about an axis to move from the position in the treatment laser beam path to the position out of the treatment laser beam path.

Alternatively, the reflex mirror is translated along an axis to move from the position in the treatment laser beam path to the position out of the treatment laser beam path.

In another form the invention resides in an ophthalmic treatment device comprising:
one or more aiming lasers producing aiming laser beams that are directed into a treatment path to a target treatment area by at least a first mirror;
a treatment laser producing a treatment laser beam that is directed into the treatment path by a second mirror;
a viewing microscope that views the target treatment area along a viewing path coaxial with the treatment path; and
a reflex mirror directing illumination from a source of illumination into an illumination path coaxial with the treatment path.

Suitably the reflex mirror is biased to maintain a position in the treatment path but is movable to a position out of the treatment path by an actuator. The reflex mirror is preferably biased by a spring and the actuator is preferably a motor. Alternatively the actuator may be a solenoid or a piezoelectric device.

In a yet further form, the invention resides in a method of performing ophthalmic laser treatment including the steps of:
illuminating a target treatment area with illumination directed coaxially along a treatment path by a reflex mirror;
directing aiming laser beams along the treatment path to the target treatment area;
viewing the target treatment area and adjusting the aiming laser beams to be aimed at a selected treatment zone; and
activating a treatment laser to produce a treatment laser beam that is directed into the treatment zone;
wherein the reflex mirror is moved out of the treatment path prior to treatment laser emission and then moves back into the treatment path after treatment laser emission ceases.

Suitably the reflex mirror is moved automatically when the treatment laser is activated and is released back to the biased position when activation of the treatment laser ceases.

Further features and advantages of the present invention will become apparent from the following detailed description.

BRIEF DESCRIPTION OF THE DRAWINGS

To assist in understanding the invention and to enable a person skilled in the art to put the invention into practical effect, preferred embodiments of the invention will be described by way of example only with reference to the accompanying drawings, in which.

DETAILED DESCRIPTION OF THE INVENTION

Figure 1:
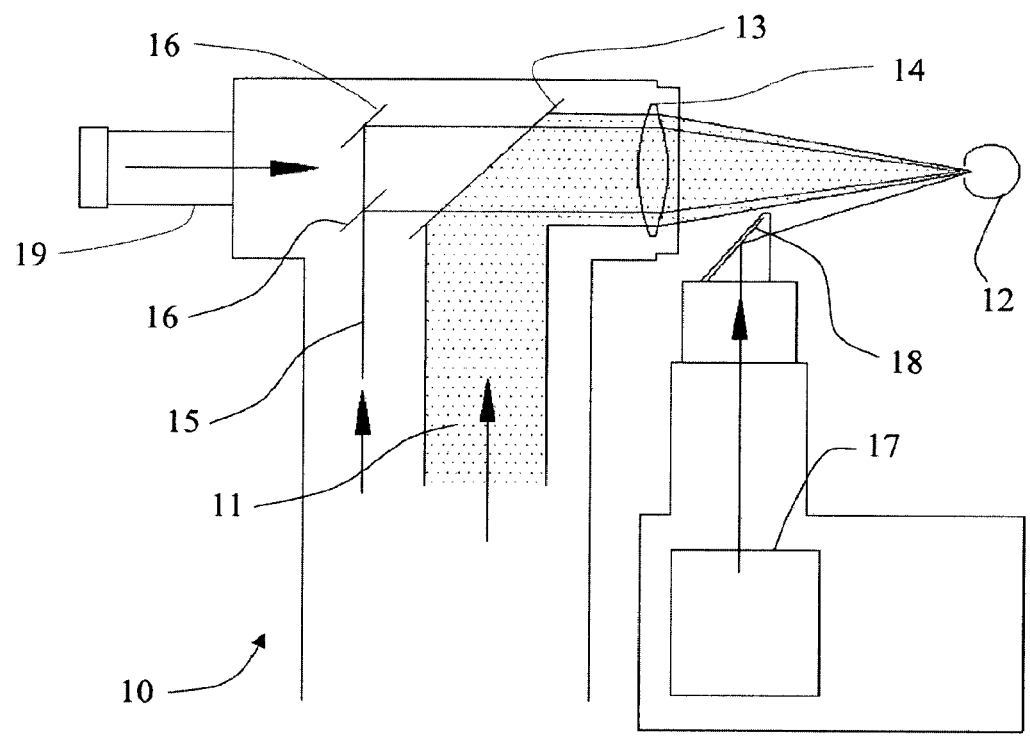
FIG. 1 is a sketch of a prior art arrangement.

Embodiments of the present invention reside primarily in ophthalmic laser device. Accordingly, the elements have been illustrated in concise schematic form in the drawings, showing only those specific details that are necessary for understanding the embodiments of the present invention, but so as not to obscure the disclosure with excessive detail that will be readily apparent to those of ordinary skill in the art having the benefit of the present description.

In this specification, adjectives such as first and second, left and right, and the like may be used solely to distinguish one element or action from another element or action without necessarily requiring or implying any actual such relationship or order. Words such as "comprises" or "includes" are intended to define a non-exclusive inclusion, such that a process, method, article, or apparatus that comprises a list of elements does not include only those elements but may include other elements not expressly listed, including elements that are inherent to such a process, method, article, or apparatus.

Referring to FIG. 1 there is shown a prior art ophthalmic slit lamp microscope laser system 10 in which a treatment laser beam 11 is directed to a targeted treatment area in an eye 12 by a mirror 13 and objective lens 14. An aiming laser beam 15 is directed by, in this case, a pair of mirrors 16 through the objective lens 14 to the same targeted treatment area in the eye 12. The dichroic mirror 13 reflects at the treatment laser wavelength but transmits at the aiming laser wavelength. A light source 17 produces broad spectrum (white) light that is directed by mirror 18 to the eye 12 from an off-axis position. The target treatment area is viewed through a microscope 19.

Figure 2:
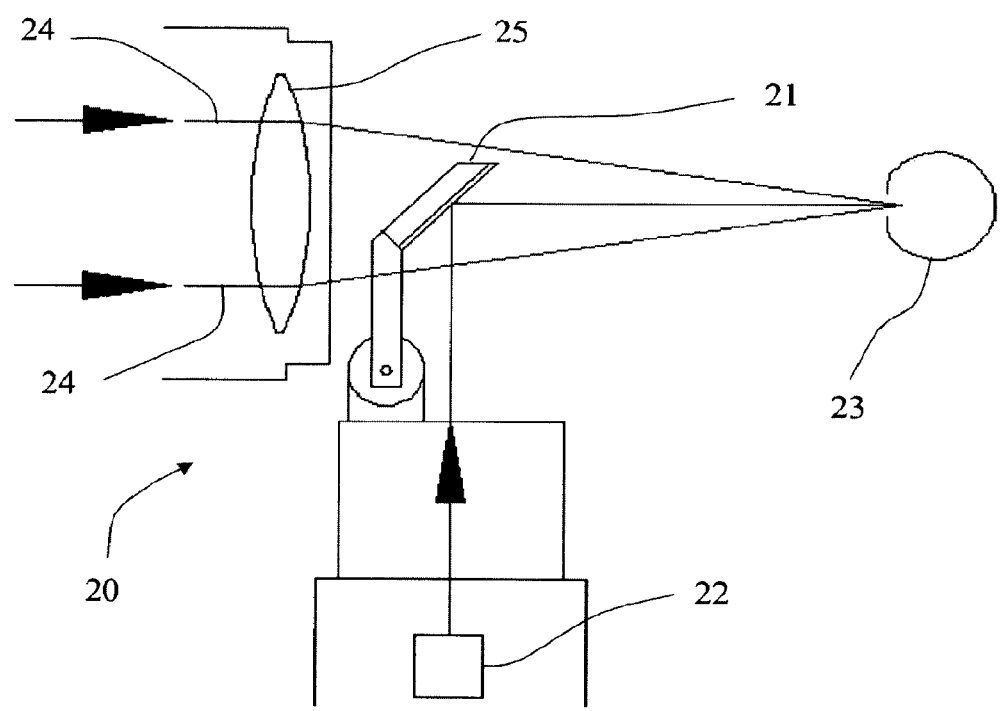
FIG. 2 is a sketch of a side view of one embodiment of the invention in a first configuration before treatment.

A side view of one embodiment of the invention is shown in FIG. 2. A reflex coaxial illuminator 20 comprises a reflex mirror 21 that directs light from a light source 22 to an eye 23. As with the prior art the light source 22 is suitably a broad spectrum (white) light source.

The mirror 21 is of a size and shape to be located between a pair of laser aiming beams 24 that are directed to the eye 23 by an objective lens 25. The user positions the aiming beams 24 by moving the slit lamp microscope system to target a treatment zone while viewing the eye through the microscope.

Figure 3:
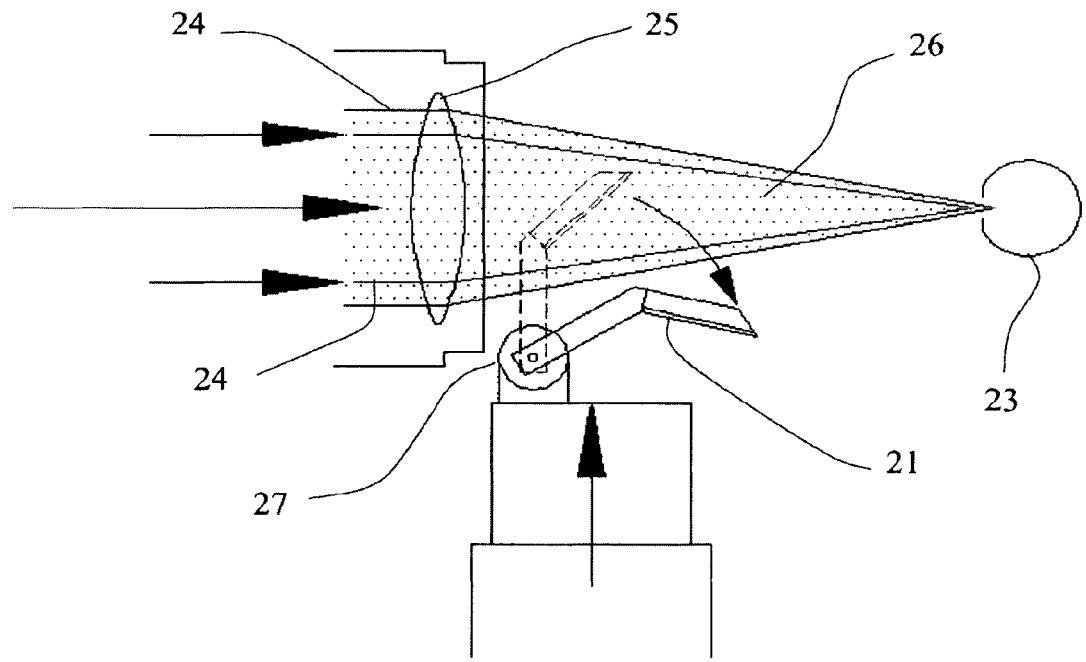
FIG. 3 is a sketch of a side view of the invention of FIG. 2 in a second configuration during emission of the treatment laser.

Referring to FIG. 3, the user then activates a treatment laser beam emission that follows a treatment path 26 through the objective lens 25 to the selected treatment zone. Upon activation of the treatment laser the reflex mirror 21 is moved out of the treatment path prior to emission by an actuator 27.

Figure 4:
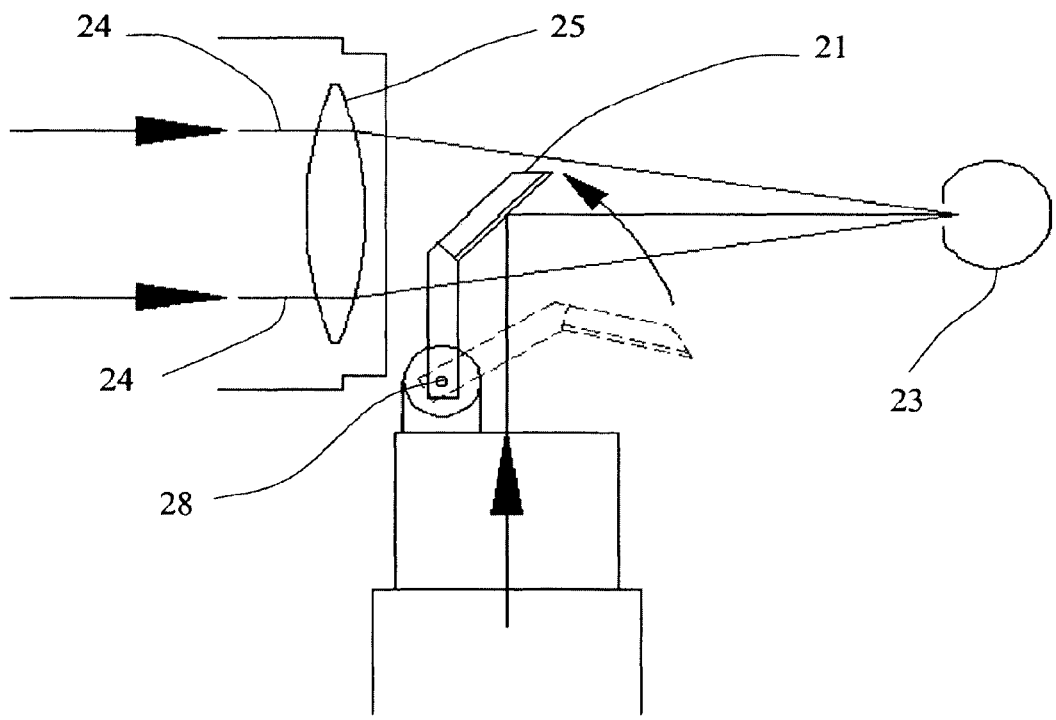
FIG. 4 is a sketch of a side view of the invention of FIG. 2 in a third configuration after treatment.

A typical treatment modality requires a short pulse from the treatment laser of around 1 msec or less. As soon as the treatment laser emission ceases the reflex mirror is immediately returned to the original position, as shown in FIG. 4. This can be achieved quickly if the reflex mirror is biased to the original position by, for example, a spring or other biasing means 28. The out-of-path time is less than 1 second and typically less than 0.2 seconds.

Figure 5:
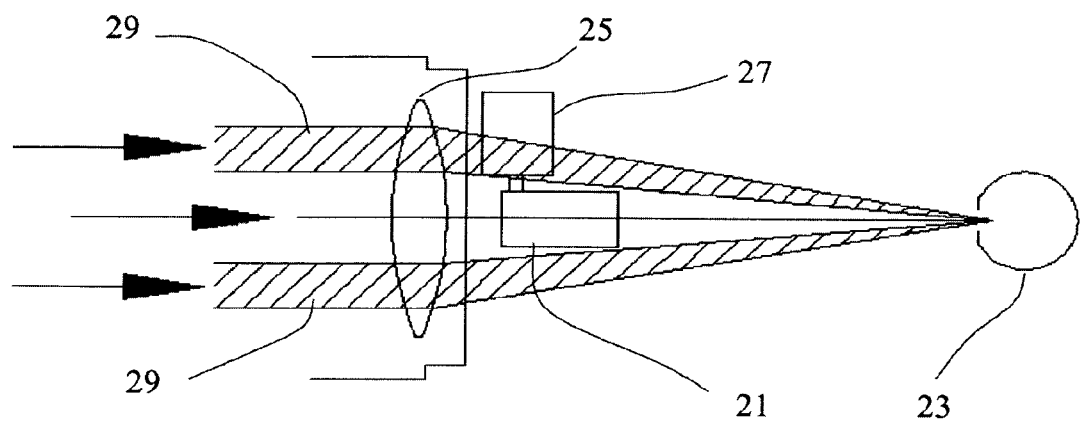
FIG. 5 is a top view of the embodiment of the invention of FIG. 2 showing a binocular viewing path.

As can be seen in the top view of FIG. 5, the reflex mirror 21 is of a size and shape to not block the viewing paths 29 of a binocular microscope. Because the reflex mirror 21 is biased by a spring to a position within the treatment path 26 but without blocking the aiming beams 24 or viewing paths 29, it permits the user to view the target treatment area under coaxial illumination and accurately direct the aiming beams to the target treatment zone. Upon activation of the treatment laser beam the mirror is moved out of the beam path prior to emission but snaps back as soon as the treatment laser ceases treatment. This can be achieved by electrical connection between the treatment laser and the actuator.

The time taken for the reflex mirror to move is very short so that the interruption to illumination is barely noticeable by a user in most cases.

Figure 6:
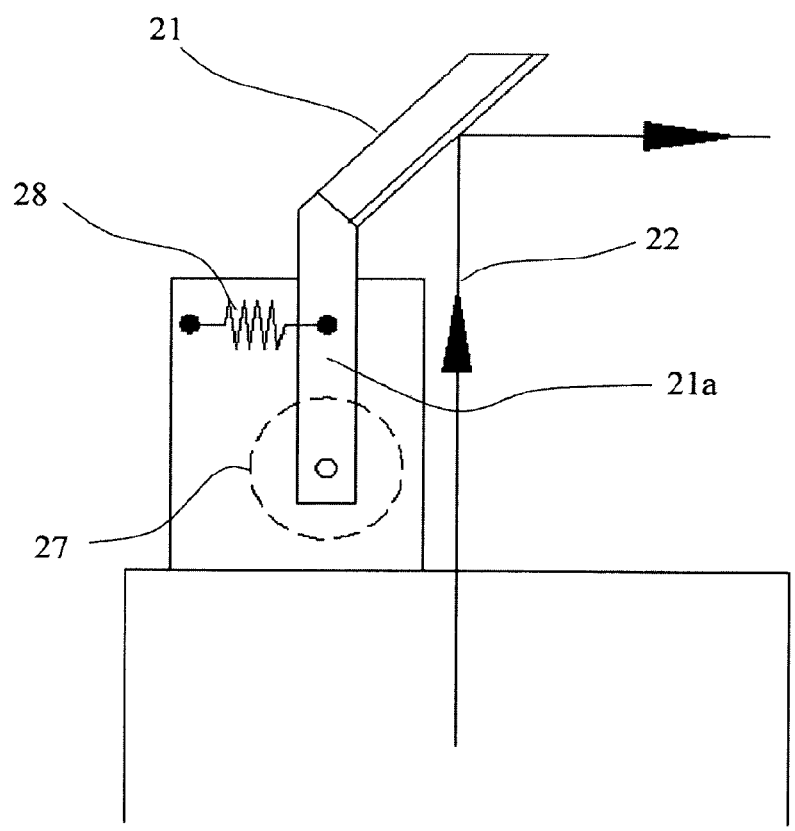
FIG. 6 shows one form of an actuator of one embodiment of the invention.

The reflex mirror can be moved by any suitable form of actuator. One form of the actuator 27 is shown in FIG. 6. In FIG. 6 the actuator 27 is a small electric motor that is activated to rotate an axle mounting the reflex mirror 21. A biasing means 28 in the form of a coil spring has one end fixed and the other end acts against a mirror arm 21a as shown in FIG. 6.

Figure 7:
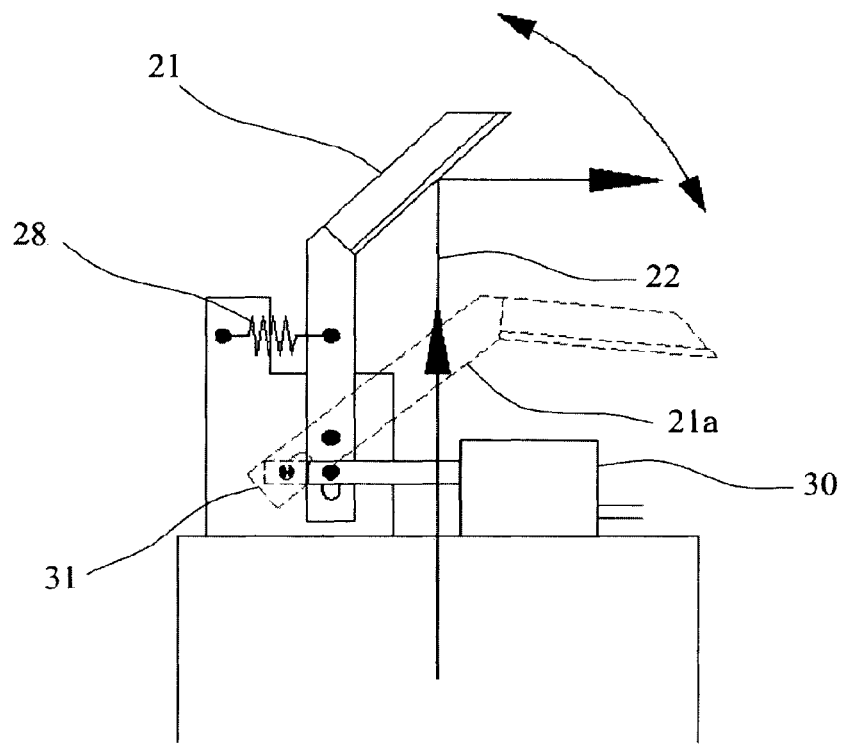
FIG. 7 shows another form of an actuator.

An alternate form of the actuator is shown in FIG. 7. In this case a linear actuator 30 acts on one end 31 of the mirror arm 21a. Upon release the biasing means 28 in the form of a coil spring acts to rotate the mirror arm 21a back to the original position, as previously described.

Figure 8:
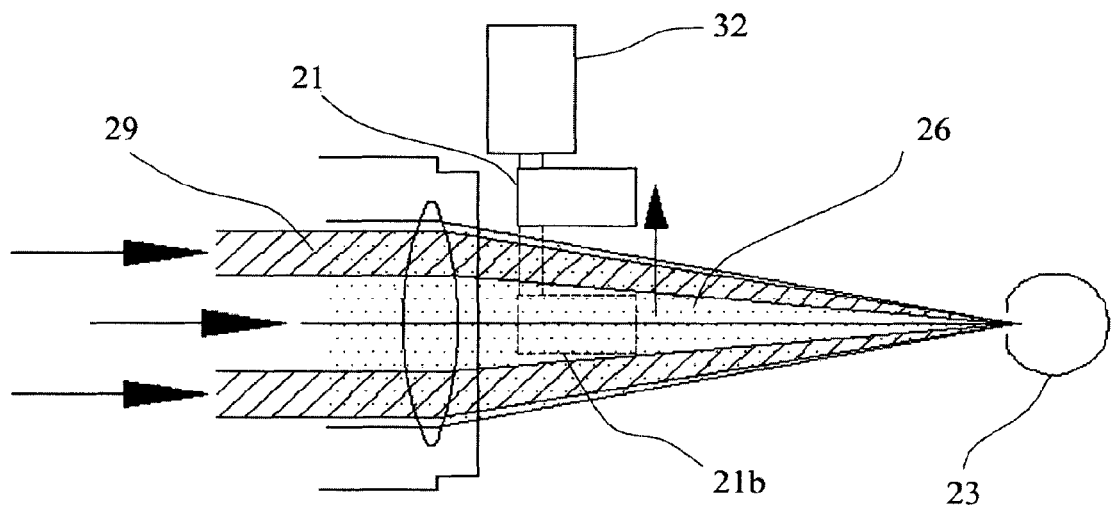
FIG. 8 shows a linear actuator.

A further form of actuator is shown in FIG. 8. In this case a linear actuator 32 translates the mirror 21 into and out of position between the binocular viewing path 29. In FIG. 8 the mirror 21 is shown out of the beam and the location in the beam is shown in dotted outline 21b.

Other forms of actuation, such as piezoelectric devices or manual actuation by a user, will also be suitable.

For an added level of safety a position sensor may be employed to detect that the reflex mirror 21 is completely out of the treatment laser beam path before the treatment laser is activated. An alternate approach is for the mirror arm 21a to close a contact to activate the treatment laser as it moves out of the treatment laser beam path.

Figure 9:
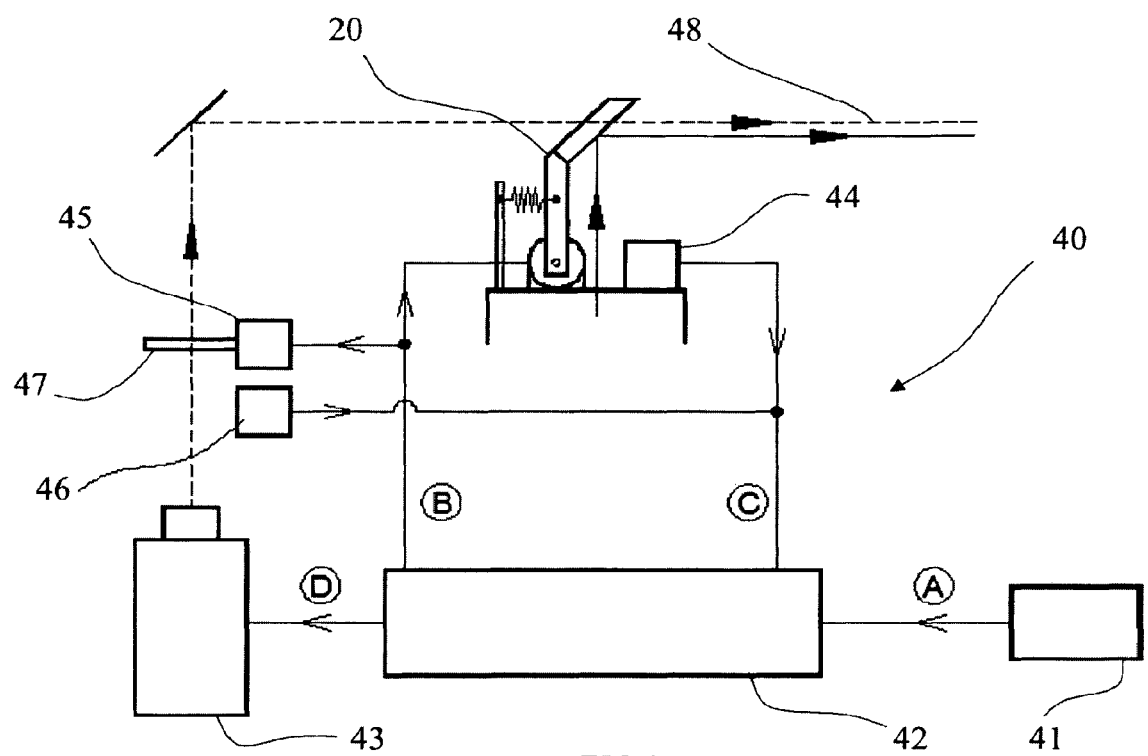
FIG. 9 shows a block diagram of an ophthalmic laser treatment system.
Figure 10:
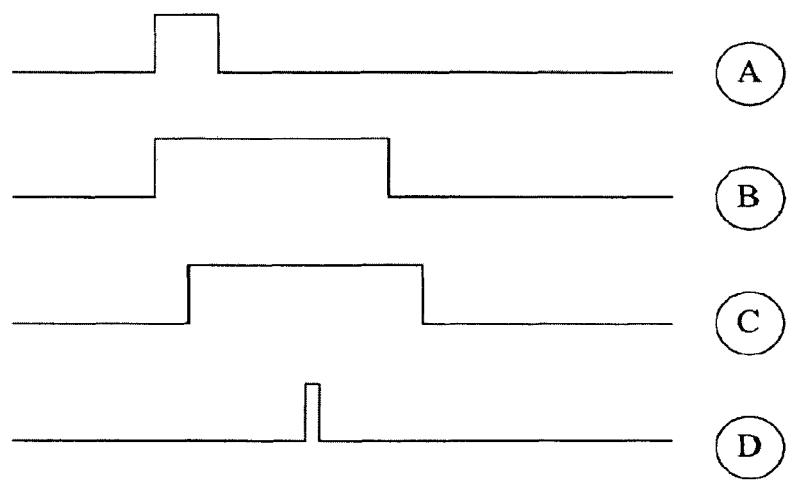
FIG. 10 shows a timing diagram for operation of the system of FIG. 9.

An ophthalmic laser treatment system 40 incorporating a reflex coaxial illuminator 20 is shown in FIG. 9 and an operation timing diagram is shown in FIG. 10. The system is activated by a treatment laser fire switch 41, which is indicated as A in the timing diagram. A system timing control circuit 42 sends a signal B to open a safety shutter 47 and actuate the reflex coaxial illuminator 20 out of the path of the treatment laser beam 48. The system timing control circuit also receives a signal C from a mirror position sensor 44 and shutter open sensor 46 that indicates that the mirror and shutter are out of the path before firing the laser system 43. The system timing control circuit 42 sends a signal D that fires a laser pulse from the laser system 43. The signal B is then switched off which releases the shutter 47 and reflex coaxial illuminator 20. A shutter closed sensor 45 provides a positive safety indication.

It will be appreciated that, unlike the prior art arrangements, the invention provides coaxial illumination of the eye without obstructing the viewing path, the aiming beams or the treatment laser path, without noticeable interruption to viewing by the user. The inventors envisage the invention finding particular application in posterior membranectomy or hyaloidotomy using an Nd:YAG laser.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this invention is intended to embrace all alternatives, modifications and variations of the present invention that have been discussed herein, and other embodiments that fall within the spirit and scope of the above described invention.

The invention claimed is:

1. A method of performing ophthalmic laser treatment with a treatment laser including the steps of:
    viewing a target treatment area in an eye of a patient using a binocular microscope, wherein the target treatment area is illuminated with illumination directed coaxially with a treatment laser beam path by a reflex mirror located in a position in the treatment laser beam path but without obstructing a viewing path from the binocular microscope to the eye coaxial with the treatment laser beam path;
    moving the reflex mirror from a position in the treatment laser beam path to a position out of the treatment laser beam path to allow a treatment laser beam from the treatment laser to pass along the treatment laser beam path;
    activating the treatment laser to produce the treatment laser beam, which is directed along the treatment laser beam path to a treatment zone within the treatment area; and
    moving the reflex mirror back into the position in the treatment laser beam path.

2. The method of claim 1 further including the steps of selecting the treatment zone by:
    directing aiming laser beams to pass either side of the reflex mirror to the target treatment area; and
    adjusting the aiming laser beams to be aimed at the treatment zone.

3. The method of claim 1, wherein the reflex mirror is biased to maintain the position in the treatment laser beam path, is moved automatically when the treatment laser is activated, and is released back to the biased position when activation of the treatment laser ceases.

4. The method of claim 1, wherein the reflex mirror is moved out of the treatment laser beam path and moved back into the treatment laser beam path without noticeable interruption to viewing by a user.

5. The method of claim 1, wherein the reflex mirror is moved out of the treatment laser beam path and moved back into the treatment laser beam path in less than 1 second.

6. The method of claim 1, wherein the reflex mirror is moved out of the treatment laser beam path and moved back into the treatment laser beam path in less than 0.2 second.

7. The method of claim 1, wherein the reflex mirror is rotated about an axis to move from the position in the treatment laser beam path to the position out of the treatment laser beam path.

8. The method of claim 1, wherein the reflex mirror is translated along an axis to move from the position in the treatment laser beam path to the position out of the treatment laser beam path.

9. The method of claim 1, wherein the reflex mirror is biased to maintain the position in the treatment laser beam path but is movable to a position out of the treatment laser beam path by an actuator.

10. The method of claim 9, wherein the reflex mirror is biased by a spring.

11. The method of claim 9, wherein the actuator is a motor.

12. The method of claim 9, wherein the actuator is a solenoid.

13. The method of claim 9, wherein the actuator is a piezoelectric device.

14. The method of claim 1 further including the step of sensing when the reflex mirror is out of the treatment laser beam path.

15. The method of claim 1, wherein the step of moving the reflex mirror is performed using a system timing control circuit that controls timing of:
    moving the reflex mirror out of the treatment laser beam path;
    sensing a signal from a position sensor that indicates the reflex mirror is out of the treatment laser beam path;
    activating the treatment laser; and
    moving the reflex mirror into the treatment laser beam path.

16. The method of claim 1, wherein the treatment is effected with an ophthalmic laser system comprising the treatment laser, the binocular microscope, an illumination device providing the illumination, and the reflex mirror, the reflex mirror being sized and shaped so as to permit binocular viewing of the eye of the patient unobstructed by the reflex mirror when the reflex mirror is in the position in the treatment path.

17. Then method of claim 1, wherein activating the treatment laser actuates the reflex mirror to move out of the treatment path and opens a safety shutter in the laser treatment beam path.

18. A reflex coaxial illuminator of an ophthalmic laser device comprising a reflex mirror translatable along an axis to move from a position in a treatment laser beam path to a position out of the treatment laser beam path, the reflex mirror being sized and shaped so as to permit binocular viewing of an eye of a patient unobstructed by the reflex mirror along a binocular viewing path coaxial with the treatment laser beam path when the reflex mirror is in the position in the treatment laser beam path,
    wherein the treatment laser beam path is between a laser device and the eye of the patient and the binocular viewing path is between a binocular microscope and the eye of the patient,
    wherein in response to the reflex mirror being in the position in the treatment laser beam path, the reflex mirror directs illumination from an illumination device into an illumination path between the reflex mirror and the eye, coaxial with the treatment laser beam path and the viewing path thereby permitting binocular viewing of the eye of the patient unobstructed by the reflex mirror, and in response to the reflex mirror being in the position out of the treatment laser beam path, a laser beam from the laser device can pass unobstructed by the reflex mirror through the treatment path to the eye of the patient.

19. The reflex coaxial illuminator of claim 18 wherein the reflex mirror is biased to maintain the position in the treatment laser beam path but is translatable to the position out of the treatment laser beam path by an actuator.

20. The reflex coaxial illuminator of claim 19 wherein the reflex mirror is biased by a spring.

21. The reflex coaxial illuminator of claim 19 wherein the actuator is a motor or a solenoid or a piezoelectric device.

22. The reflex coaxial illuminator of claim 18 wherein the reflex mirror is a non-transmissive reflex mirror.

\* \* \* \* \*